United States Patent [19]
Stockel et al.

[11] Patent Number: 4,680,286
[45] Date of Patent: Jul. 14, 1987

[54] USE OF SELENIUM-CONTAINING COMPOUNDS FOR NEGATING THE TOXIC EFFECTS OF GOLD COMPOUNDS USED IN THE TREATMENT OF RHEUMATOID ARTHRITIS, AND A NOVEL SELENIUM-CONTAINING GOLD COMPOUND AND USE THEREOF AS AN ANTI-RHEUMATOID ARTHRITIS MEDICINE

[76] Inventors: Richard F. Stockel, 457 Rolling Hills Rd., Bridgewater, N.J. 08807; Phillip E. Dumas, 137 Louise Dr., Morrisville, Pa. 19067

[21] Appl. No.: 735,424

[22] PCT Filed: Aug. 10, 1983

[86] PCT No.: PCT/US83/01239
§ 371 Date: Apr. 9, 1985
§ 102(e) Date: Apr. 9, 1985

Related U.S. Application Data

[63] Continuation-in-part of Ser. No. 347,708, Feb. 11, 1982, abandoned.

[51] Int. Cl.$^4$ .................. A61K 31/70; C07H 23/00
[52] U.S. Cl. .................................... 514/23; 536/121
[58] Field of Search ........................ 536/121; 514/23

[56] References Cited
U.S. PATENT DOCUMENTS
4,096,250  6/1978  Hill ..................................... 536/121

Primary Examiner—Stanley J. Friedman
Attorney, Agent, or Firm—Armstrong, Nikaido, Marmelstein & Kubovcik

[57] ABSTRACT

The toxic effects of gold compounds used in the treatment of rheumatoid arthritis can be negated by the use of a selenium-containing compound. A new selenium-containing gold compound has been found to be useful as a gold compound type anti-rheumatoid arthritis medicine which can self-detoxify gold toxicity.

5 Claims, No Drawings

USE OF SELENIUM-CONTAINING COMPOUNDS FOR NEGATING THE TOXIC EFFECTS OF GOLD COMPOUNDS USED IN THE TREATMENT OF RHEUMATOID ARTHRITIS, AND A NOVEL SELENIUM-CONTAINING GOLD COMPOUND AND USE THEREOF AS AN ANTI-RHEUMATOID ARTHRITIS MEDICINE

This application is a continuation-in-part of our U.S. patent application Ser. No. 347,708 filed on Feb. 11, 1982 now abandoned.

The present invention relates to a method of negating the toxic effects of gold compounds. More particularly, the present invention relates to a method of negating the toxic effects of gold compounds used in the treatment of rheumatoid arthritis, which method comprises administering to a patient a selenium-containing compound. The present invention is also concerned with a novel selenium-containing gold compound which can be effectively used as a so-called gold compound type anti-rheumatoid arthritis medicine which can self-detoxify gold toxicity.

The most common form of chronic inflammatory arthritis is rheumatoid arthritis, which is characterized by symmetrical inflammatory polyarthritis, morning stiffness and positive rheumatoid factor. Over more than 100 diseases have been classified as arthritis, in addition to chronic inflammatory arthritis.

Each decision to treat with a drug requires careful therapeutic weighing of the hazards and the benefits of the drug versus the disability caused by the symptoms. Various groups of drugs useful for arthritis include salicylates, indole derivatives, propionic acid derivatives, phenylbutazone and oxyphenbutazone, penicillamine, corticosteroids, cytotoxic drugs and anti-gout agents. For an excellent review on these anti-arthritic drugs, a review article written by J. A. Markenson, appearing in Drug Therapy, January, 1981, page 45 dives a comparative overview of these types of classes of drugs. As mentioned above, there are various drugs effective in the treatment of arthritis, however, gold compounds used in gold therapy are most effective as anti-rheumatoid agents, and the gold therapy should be considered in patients with active disease who fail to respond to the plethora of drugs previously mentioned to reduce inflammation.

Active adult and juvenile rheumatoid arthritis are the principal indications where administration of these agents are used, but beneficial effects have also been obtained in some patients with psoriatic arthritis. Although their exact mechanism of action is unknown, the gold compounds exert an anti-inflammatory effect in these disorders, and unlike other anti-arthritic drugs may affect the course of the disease.

There are essentially four kinds of gold compound type anti-rheumatoid agents in the marketplace which are used in gold therapy. One of the first anti-rheumatic compounds was gold sodium thiomalate. Preparation of this compound can be found in U.S. Pat. No. 1,994,213. Other gold containing drugs are 1-thio-D-glucopyranosato gold and [[(phenylcarbamoyl)methyl]-thio] gold. Preparation of the latter compound can be found in U.S. Pat. No. 2,451,841. The fourth drug is known chemically as (2,3,4,6-tetra-O-acetyl-1-thio-$\beta$-D-glucopyranosato-S-triethylphosphine) gold. U.S. Pat. Nos. 3,635,945 and 3,708,579 describe the preparation and use of this drug. These four gold compounds offer various degrees of relief in rheumatoid arthritis.

The gold therapy using the gold compounds as described above is effective in the treatment of rheumatoid arthritis, but is accompanied by side effects. Therefore, the gold compounds should be used with extreme cautions. In order to be effective, high doses of gold compounds are required. General method of administering to a patent gold compounds in the treatment of rheumatoid arthritis is described below.

In adults the initial single weekly injections of 10 mg are given the first week, 25 mg the second week, 25 or 50 mg the third week and 50 mg each week thereafter until a total dosage of 800 mg to 1 g has been administered. If there is no response after 1 g has been given, the drug should be discontinued. If the patient has improved and no toxic effects have been developed, dosage can be reduced to 50 mg every two weeks for 4 doses, every three weeks for 4 doses, and then monthly. A remission after one year of maintenance therapy has been considered as an indication for complete withdrawal of the drug, but many physicians now feel that gold therapy probably can continue indefinitely, on a reduced dosage schedule. If relapse occurs when the interval between doses is increased, or the drug is discontinued, the former schedule should be reinstituted. For children, the recommended dosages involve 1 mg/kg of body weight weekly for 20 weeks and the same dose at 2 to 4 week intervals thereafter for as long as therapy is beneficial and there are no signs of toxicity. Single dosages for children and all but the largest adolescent should not exceed 25 mg. For an excellent review on gold compounds in rheumatoid arthritis, the article by J. D. O'Duffy, appearing in Drug Therapy, March, 1979, page 61, should be consulted.

As described before, it is known that gold therapy is effective in the treatment of rheumatoid arthritis but is accompanied by side effects. In this connection, the Arthritis Foundation publishes a brochure on gold treatment in rheumatoid arthritis and it clearly states that this method of treatment involves numerous risks and precautions. Dermatitis and lesions of the mucous membranes are common and may be serious. Hematologic reactions are observed in many cases; in fact, some fatalities have been attributed to this treatment. Effects on the kidney range from proteinuria to nephrotic syndrome. Cholestatic jaundice has also been reported in some cases.

Pruritus may signify the early development of a skin reaction. When a pruritic skin lesion occurs, whose etiology is not certain, it appears gold therapy must be discontinued immediately, for another dose may produce a much more severe skin reaction. Anaphylactoid reactions may also occur with gold therapy, but they are probably caused as much by the vehicle, as is caused by the gold compounds. Nausea, vomiting and weakness sometimes result from this treatment. Toxic effects may be observed after the first injection, during the course of therapy, or several months after gold therapy has been discontinued. Their incidence in severity appear to depend upon dosage. Although they may occur at any time, severe toxic effects of the gold compounds are most common after 300 to 500 milligrams have been administered. Since the occurrence of these reactions is unpredictable, patients should be questioned about symptoms of toxicity prior to each injection. A complete blood count, including platelet estimation should be performed every two to three weeks after the first 6 months and less often with decreasing dosage. Qualitative urine protein tests should be performed before every injection. If toxicity develops, gold therapy should be discontinued immediately. Treatment with topical or systemic corticosteroids may be necessary and the chelating agent, dimercaprol, may be used to increase excretion of gold.

Gold compounds should be used with extreme cautions in patients with impaired renel or hepatic function, blood disorders, skin rash or marked hypertension. They are contraindicated in patients with severe debilitation, systemic lupus erythematosus, or previous signs of gold toxicity. They are seldom needed during pregnancy but if their use is contemplated, the benefit/risk ratio should be considered. Diabetes mellitus or congestive heart failure should be under control before initiating gold therapy.

It is generally recommended that the gold therapy be not given until other therapy is first considered because, as mentioned above, the gold therapy involves numerous risks and precautions. When properly supervised by a knowledgeable physician, in about 2 out of 10 patients who are treated early in the course of the disease, the treatment has to be discontinued because of side effects of the gold, and one or two of every 10 patients received no benefit whatsoever. However, an average of about 7 out of 10 patients who are treated early in the course of the disease experience a good or excellent result. These facts show that the gold therapy is an effective therapy.

However, it is necessary to reduce the potential serious side effect of the gold therapy. In order to lessen potential serious side effects of this therapy, urine tests are done to make sure that no damage has occurred from preceding dosages. Occasionally, the blood is tested for urea content.

A potential problem is the possibility of damage to the bone marrow, the place where the body manufactures its red blood cells and white blood cells. To guard against this, as mentioned above, a blood sample is examined for its hemoglobin content and white blood cell count.

Another side effect is the possibility of a skin rash. When this occurs it is almost always itchy and usually also red and scaly, with tiny bumps. They may appear anywhere on the body, or even inside the mouth; but the most frequent locations are the chest, arms and legs. This rash can be quite severe and uncomfortable at times.

Liver damage and intestinal cramps or diarrhea have also been reported in patients treated with gold but these reactions are extremely rare. However, a blood sample is analyzed every few months to detect any possible threat of liver damage.

If any of these reactions develop, gold treatment is interrupted immediately. It may take several months for the gold to be eliminated from the body but fortunately, complete recovery from the side effect usually occurs. In the meantime, if the reaction is severe, it may be treated with cortisone or compounds which speed elimination of gold from the body. Finally, some patients receiving gold therapy complain of metallic taste in the mouth, small sores in the mouth or thinning out of the hair. When this happens, it is generally wise to reduce the dosage of gold and usually these symptoms go away.

As mentioned above, the gold therapy is effective in the treatment of rheumatoid arthritis, but has a significant drawback such that the gold therapy is often accompanied by serious side effects. Therefore, the use of the gold therapy is limited. Due to the above-mentioned sometimes very severe side effects, any treatment that would negate these unforseen problems in gold therapy, would be of enormous assistance in combating rheumatoid arthritis.

The present inventors have made extensive and intensive studies in order to obtain a medicine excellent in detoxification effect against the gold toxicity. As a result, the present inventors have found that selenium-containing compounds has excellent effects of detoxification against the gold toxicity. Further, the present inventors have made extensive and intensive studies with a view to obtaining so-called gold compound type anti-rheumatoid arthritis medicine which possesses a self-detoxification effect against the gold toxicity resulting from the gold therapy of rheumatoid arthritis but does not sacrifice the anti-rheumatoid arthritis activity. As a result, the present inventors have found that a novel selenium-containing gold compound of the later-mentioned formula (1) can be effectively used as a gold compound type anti-rheumatoid arthritis medicine which is not only effective in the treatment of rheumatoid arthritis but also possesses a self-detoxification effect against the gold toxicity. The present invention has been completed based on the above.

With respect to selenium, it is known that selenium has protective effects against several heavy metals in numerous biological systems ("Biochemical Effects of Environmental Pollutants", Chapter 21, entitled "Metabolic Interactions of Selenium with Heavy Metals" by R. A. Rimerman, D. R. Buhler and P. D. Whanger).

Although the mechanism in which selenium negates heavy metal toxicity is unknown, there are many studies which indicate or suggest possible mechanisms. These include: selenium-metal binding, selenium-metal or selenium-metal protein aggregation, enhancement of immune response by selenium, tissue/or sub-cellular redistribution of metal by selenium, selenium induced shift of metal among soluble cytosol proteins, selenium requirement in metal excretion and enhanced reduced metabolism of metal, for example, in the demethylation of metal mercury cation.

Protection of selenium against heavy metal toxicity was first shown by A. B. Kar, R. P. Das and F. Mukerji, Proc. Nat. Inst. Soc. India, 26,40 (1960), who observed that selenium prevents cadmium-induced testicular demage. Protection effects of selenium against the toxicity of mercury, silver and thallium have been subsequently observed by other researchers. However, the mechanisms of detoxification of the above-mentioned heavy metals by selenium are complicated are not identical for all the metals or all forms of the same metals. Mechanisms may involve a direct binding between selenium and the heavy metal; a direct binding between selenium metal and other small molecules or macromolecules; or an indirect stoichiometric or catalytic effect of selenium mediated by other molecules, such as an enzyme.

As mentioned above, it is known that selenium has protective effects against the toxicity of several specific heavy metals. However, it is not known at all that a selenium-containing compound has a detoxification effect against the gold toxicity, and as mentioned before, the present inventors have found for the first time that the selenium-containing compound has an excellent detoxification effect against the gold toxicity.

It is, accordingly, an object of the present invention to provide a method of negating the toxic effects of gold compounds used in the treatment of rheumatoid arthritis, which comprises administering to a patient a selenium-containing compound.

Another object of the present invention is to provide a novel selenium-containing gold compound which can be effectively used as a gold compound type anti-rheumatoid arthritis medicine which can self-detoxify gold toxicity.

The foregoing and other objects, features and advantages of the present invention will be apparent from the following detailed description.

In one aspect of the present invention, there can be provided a method of negating the toxic effects of gold compounds, which comprises administering to a patient an effective amount of a selenium-containing compound adapted to negate the toxic effects of gold compounds used in the treatment of rheumatoid arthritis.

As the selenium-containing compounds to be used in the present invention, there can be mentioned an alkali metal salt of selenious acid, an alkali metal salt of selenic acid, a selenoamino acid, an $\omega$-selenocarboxylic acid, a selenocarbohydrate, selenium yeast and a protein containing selenium. These selenium-containing compounds are effective for negating the gold toxicity resulting from the gold therapy especially of rheumatoid arthritis.

As the alkali metal salt of selenious acid to be used in the present invention, there may mentioned sodium selenite. As the alkali metal salt of selenic acid, there may be mentioned sodium selenate. As the selenoamino acid to be used in the present invention, there may be mentioned amino acids containing selenium which has replaced sulfur in the thio or disulfide groups of sulfur-containing amino acids such as selenomethionine, selenocysteine, Semethylselenocysteine, selenocystine and selenohomomethionine. As the $\omega$-selenocarboxylic acid there may be mentioned compounds of the formula $HSe(CH_2)_nCOOH$ (where $n>5$). As the selenocarbohydrate there may be mentioned seleno(tetra-O-acetyl-1-$\beta$-D-glucopyranosyl) and seleno(1-$\beta$-D-glucopyranosyl). As the protein containing selenium, there may be mentioned proteins containing selenium which has replaced sulfur in the thio or disulfide groups of sulfur-containing amino acids. The above mentioned selenium-containing compounds are known.

The selenium-containing compounds to be used in the present invention can be administered orally or parenterally, for example, in the form of an intravenous injection, a hypodermical injection or a suppository. The dosage may vary depending upon ages, severities and body weights of patients, but a selenium-containing compound as an active ingredient may be usually administered in a daily dose of from about 1 to about 500 mg for adults, if necessary, in divided dosage forms. The selenium-containing compounds to be used in the present invention can be used concomitant with the gold therapy of rheumatoid arthritis, or alternatively the selenium-containing compounds can be administered prior to treatment with the gold compounds to build up levels of selenium in the body that will mitigate the toxic side effects of the gold compounds. Even though selenium itself at high levels in the body can be toxic, the body can tolerate low levels and the selenium compounds can detoxify gold poisoning particularly in the renal system and liver, where gold concentrates after gold therapy.

In the present invention, the selenium-containing compound as such may be administered. However, a pharmaceutical composition which comprises a selenium-containing compound as an active ingredient is usually administered. The composition or preparation may be in the form of, for example, capsule, granule, powder, tablet, pill, ointment, syrup, injection, suppository or the like. As the pharmaceutical agents to be used in the pharmaceutical composition, there may be mentioned excipients such as white sugar, lactose, glucose, starch, corn starch, mannite, sorbite, cellulose, talc, cyclodextrin and the like; binding agents such as cellulose, methylcellulose, hydroxypropylcellulose, hydroxy-propylmethylcellulose, polyvinyl pyrrolidone, gelatin, gum arabic, polyethylene glycol, white sugar, starch and the like; disintegrators such as starch, carboxymethylcellulose, calcium salts of carboxymethylcellulose and the like; lubricants such as talc and the like; preservatives such as sodium benzoate, sodium bisulfite and the like; suspending agents such as methylcellulose, aluminum stearate, magnesium stearate and the like; and bases such as polyethylene glycol, Witepsol, white petrolatum and the like. According to the kinds of forms of the pharmaceutical composition, appropriate pharmaceutical agents are used. Examples of the pharmaceutical compositions are given as follows.

| Composition 1 | |
| --- | --- |
| sodium selenite | 6.3 mg |
| lactose | 20.3 mg |
| corn starch | 7.0 mg |
| hydroxypropylcellulose | 1.4 mg |
| carboxymethylcellulose calcium | 1.1 mg |
| magnesium stearate | 0.2 mg |
| Composition 2 | |
| sodium selenate | 6.3 mg |
| hydroxypropylmethylcellulose | 8.0 mg |
| crystalline cellulose | 76.0 mg |
| carboxymethylcellulose calcium | 64.0 mg |
| magnesium stearate | 4.0 mg |
| Composition 3 | |
| selenomethionine | 4.0 mg |
| lactose | 178.0 mg |
| corn-starch | 37.0 mg |
| talc | 5.0 mg |

The gold toxicity-negating effect of the selenium-containing compounds was affirmed by the animal experiments using mice. The method of negating gold toxicity of the present invention will be illustrated in more detail by way of Examples later.

In another aspect of the present invention, there is provided a novel selenium-containing gold compound which can be effectively used as a gold compound type anti-rheumatoid arthritis medicine which can self-detoxify gold toxicity, and which has the following general formula:

$$(R_2)_3P \rightarrow Au-Se-R_1 \qquad (1)$$

wherein
R$_1$ stands for
an unsubstituted or substituted glucose radical,
an unsubstituted or substituted malic acid radical,
an unsubstituted or substituted malate radical, or
an unsubstituted or substituted phenylcarbamoylmethy radical; and
R$_2$ stands for a linear or branched alkyl group having 1 to 4 carbon atoms.

The unsubstituted or substituted glucose radical in the above general formula (1) is represented by the following general formula:

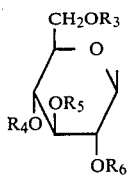
(2)

(wherein $R_3$, $R_4$, $R_5$, and $R_6$ each independently stand for H, an acetyl group, a propionyl group or a butyryl group). Specific examples of the selenium-containing gold compound represented by the formula (1) in which $R_1$ stands for an unsubstituted or substituted glucose radical of the formula (2) include (tetra-O-acetyl-1-β-D-glucopyranosyl)seleno (triethylphosphine) gold and (1-β-D-glucopyranosyl)seleno (triethylphosphine) gold. The former compound is given when $R_1$ in the formula (1) stands for a 2, 3, 4, 6-tetra-O-acetyl-1-β-D-glucopyranosyl radical represented by the formula

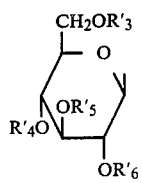
(3)

(wherein $R'_3$, $R'_4$, $R'_5$, and $R'_6$ each stand for an acetyl group), and $R_2$ in the formula (1) stands for an ethyl group. The latter compound is given when $R_1$ in the formula (1) stands for a 1-β-D-glucopyranosyl radical represented by

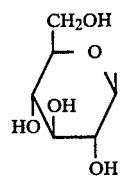
(4)

and $R_2$ in the formula (1) stands for an ethyl group.

The unsubstituted or substituted malic acid radical (radical A) or the unsubstituted or substituted malate radical (radical S) in the above general formula (1) is represented by the following general formula:

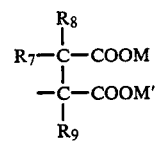
(5)

(wherein $R_7$, $R_8$ and $R_9$ each independently stand for H or an alkyl group having 1 to 4 carbon atoms and M and M' each stand for H for radical A or an alkali metal for radical S).

Specific examples of the selenium-containing gold compound represented by the formula (1) in which $R_1$ stands for an unsubstituted or substituted malate radical of the formula (5) include triethylphosphine gold sodium selenomalate. This compound is given when $R_1$ in the formula (1) stands for sodium malate radical represented by

(6)

and $R_2$ in the formula (1) stands for an ethyl group.

The unsubstituted or substituted phenylcarbamoylmethyl radical in the formula (1) is represented by the following general formula:

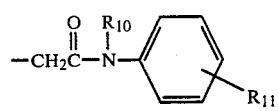
(7)

(wherein $R_{10}$ and $R_{11}$ each independently stand for H or an alkyl group having 1 to 4 carbon atoms). Specific examples of the selenium-containing gold compound represented by the formula (1) in which $R_1$ stands for an unsubstituted or substituted phenylcarbamoylmethyl radical of the formula (7) include [(phenylcarbamoyl)methyl]seleno (triethylphosphine) gold. This compound is given when $R_1$ in the formula (1) stands for a phenylcarbamoylmethyl radical represented by the formula

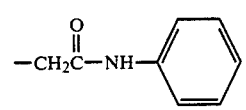
(8)

and $R_2$ in the formula (1) stands for an ethyl group.

The selenium-containing gold compound of the present invention having the formula (1) as mentioned hereinbefore is a novel and unknown compound. The method for preparing the selenium-containing gold compound according to the present invention will be described below.

The selenium-containing gold compound represented by the above-mentioned general formula (1) wherein $R_1$ stands for an unsubstituted or substituted glucose radical and $R_2$ stands for a linear or branched alkyl group having 1 to 4 carbon atoms can be prepared as follows. A halogen derivative of an acylglucose represented by the formula

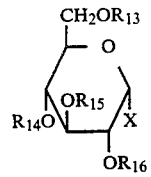
(9)

(wherein $R_{13}$, $R_{14}$, $R_{15}$ and $R_{16}$ stands for H, an acetyl group, a propionyl group or a butyryl group, and X stands for a halogen) is reacted with selenourea according to the method as described in Wagner, G. and Nuhn, P., Arch. Pharm., 297, 461 (1964) to obtain a corresponding derivative of selenoisourea. For example, an acylbromoglucose is reacted with selenourea to form an acylglucose selenoisourea hydrobromide. The above-mentioned reaction is carried out in a ketone as a reaction solvent such as acetone, methylethylketone or the like at room temperature to 100° C., generally at the boiling point of the solvent to be employed, for 10 minutes to 5 hours. Selenourea may be employed in an amount of about one equivalent to an acylbromoglucose. The thus formed selenoisourea derivative (acylglucose selenoisourea hydrobromide) is reacted with trialkylphosphine gold chloride [ClAuP(R)$_3$, wherein R stands for a linear or branched alkyl group having 1 to 4 carbon atoms] according to the method of Sutton et al [M. Sutton, E. McGurty, D. Walz and M. DiMartino, "J. of Med. Chem." 15, 1095 (1975)] to obtain the intended selenoacylglucose trialkylphosphine gold compound. Detailedly described, an acylglucose selenoisourea hydrobromide is dissolved in an aqueous solution containing 1.0 to 1.5 moles of potassium carbonate relative to one mole of the acylglucose selenoisourea hydrobromide, and then subjected to reaction with a trialkylphosphine gold chloride of an equimolar amount to the acylglucose selenoisourea hydrobromide, there by to prepare the intended selenoacylglucose trialkylphosphine gold compound. The above-mentioned reaction is carried out at $-20°$ C. to room temperature. In the above-mentioned action, the trialkylphosphine gold chloride may be dissolved in an alcohol such as ethanol, methanol and isopropanol, which contains a small amount of methylene chloride, and subjected to the reaction. The reaction time is 30 minutes to 5 hours. The thus obtained selenoacylglucose trialkylphosphine gold compound may be deacylated using an excess amount of sodium methoxide in methanol, thereby to obtain the intended selenoglucose trialkylphosphine gold compound.

The selenium-containing gold compound represented by the above-mentioned general formula (1) wherein R$_1$ stands for an unsubstituted or substituted malic acid radical, or an unsubstituted or substituted malate radical and R$_2$ stands for a linear or branched alkyl group having 1 to 4 carbon atoms can be prepared as follows. A halogen derivative of an unsubstituted or substituted malic acid is reacted with selenourea according to the above-mentioned method of Wagner to obtain a derivative of selenoisourea. For example, an unsubstituted or substituted 2-bromo-2-deoxy-malic acid is reacted with selenourea, thereby to form an unsubstituted or substituted malic acid selenoisourea hydrobromide. The above-mentioned reaction is carried out in a ketone as a reaction solvent such as acetone, methylethylketone or the like at room temperature to 100° C., generally at the boiling point of the solvent to be employed, for 10 minutes to 5 hours. Selenourea may be employed in an amount of about one equivalent to an unsubstituted or substituted 2-bromo-2-deoxy-malic acid. The thus formed selenoisourea derivative (an unsubstituted or substituted malic acid selenoisourea hydrobromide) is reacted with a trialkyl-phosphine gold chloride [ClAuP(R)$_3$, wherein R stands for a linear or branched alkyl group having 1 to 4 carbon atoms], thereby to obtain the intended unsubstituted or substituted selenomalic acid trialkylphosphine gold compound. Detailedly described, the unsubstituted or substituted malic acid selenoisourea hydrobromide is dissolved in an aqueous solution containing potassium carbonate in a molar amount of 1 to 2.5 times that of the unsubstituted or substituted malic acid selenoisourea hydrobromide and subjected to reaction with a trialkylphosphine gold chloride of an equimolar amount to the unsubstituted or substituted malic acid selenoisourea hydrobromide, thereby to obtain the intended unsubstituted or substituted selenomalic acid trialkylphosphine gold compound. The above-mentioned reaction is carried out at $-20°$ C. to room temperature. In the above-mentioned reaction, trialkylphosphine gold chloride may be dissolved in an alcohol such as ethanol, methanol or isopropanol, which contains a small amount of methylene chloride, and subjected to the reaction. The reaction time is 30 minutes to 5 hours. The thus formed unsubstituted or substituted selenomalic acid trialkylphosphine gold compound may be reacted with an alkali metal salt such as Na$_2$CO$_3$ in water according to the customary method, thereby to obtain an unsubstituted or substituted selenomalate trialkyl-phosphine gold compound.

The selenium-containing gold compound represented by the above-mentioned general formula (1) wherein R$_1$ stands for an unsubstituted or substituted phenylcarbamoylmethyl radical and R$_2$ stands for a linear or branched alkyl group having 1 to 4 carbon atoms can be prepared as follows. An unsubstituted or substituted phenylcarbamoylmethyl halogen derivative is reacted with selenourea according to the method of Wagner as mentioned before, thereby to obtain a corresponding derivative of selenoisourea. For example, an unsubstututed or substituted phenylcarbamoylmethyl bromide is reacted with selenourea, thereby to form a corresponding derivative of selenoisourea (an unsubstituted or substituted phenylcarbamoylmethyl selenoisourea hydrobromide). The above-mentioned reaction is carried out in a ketone as a reaction solvent such as acetone, methylethylketone or the like at room temperature to 100° C., generally at the boiling point of the solvent to be employed, for 10 minutes to 5 hours. Selenourea may be employed in an amount of about one equivalent to the unsubstituted or substituted phenylcarbamoylmethyl bromide. The thus formed selenoisourea derivative (an unsubstituted or substituted phenylcarbamoylmethyl selenoisourea hydrobromide) is reacted with a trialkylphosphine gold chloride [ClAuP(R)$_3$, wherein R stands for a linear or branched alkyl group having 1 to 4 carbon atoms] according to the method of Sutton et al as mentioned above, thereby to obtain the intended unsubstituted or substituted selenophenylcarbamoylmethyl trialkylphosphine gold compound. Detailedly described, an unsubstituted or substituted phenylcarbamoylmethyl selenoisourea hydrobromide is dissolved in an aqueous solution containing potassium carbonate in a molar amount of 1 to 1.5 times that of the unsubstituted or substituted phenylcarbamoylmethyl selenourea hydrobromide, and then subjected to reaction with a trialkylphosphine gold chloride of an equimolar amount to the unsubstituted or substituted phenylcarbamoylmethyl selenoisourea hydrobromide, thereby to obtain the intended unsubstituted or substituted selenophenylcarbamoylmethyl trialkylphosphine gold compound. The above-mentioned reaction is carried out at $-20°$ C. to room temperature. In the above-mentioned reaction, the trialkylphosphine gold chloride may be dissolved in an alcohol such as ethanol, methanol, isopropanol or the like, which contains a small amount of methylene chloride, and then subjected to the reaction. The reaction time is 30 minutes to 5 hours.

In a further aspect of the present invention, there is provided a method of treating a patient suffering from rheumatoid arthritis, which comprises administering to a patient an effective amount of the selenium-containing gold compound of the formula (1) as defined above. The selenium-containing gold compound of the present invention represented by the above-mentioned general formula (1) can be effectively used as a gold compound type anti-rheumatoid arthritis medicine which can self-detoxify gold toxicity. The selenium-containing gold compound of the present invention can be administered orally or parenterally, for example, in the form of an intravenous injection, a hypodermical injection or suppository. The dosage may vary depending upon ages, severities and body weights of patients, but a selenium-containing gold compound as an active ingredient may be usually administered in a daily does of from about 1 to about 500 mg for adults, if necessary, in divided dosage forms.

In the present invention, the selenium-containing gold compound as such may be administered. However, a pharmaceutical composition which comprises a selenium-containing gold compound as an active ingredient is usually administered. The composition or preparation may be of the form of, for example, capsule, granule, powder, tablet, pill, ointment, syrup, injection, suppository or the like. As the pharmaceutical agents to be used in the pharmaceutical composition, there can be mentioned excipients such as white sugar, lactose, glucose, starch, corn starch, mannite, sorbite, cellulose, talc, cyclodextrin and the like; binding agents such as cellulose, methylcellulose, hydroxypropylcellulose, hydroxypropylmethylcellulose, polyvinyl pyrrolidone, gelatin, gum arabic, polyethylene glycol, white sugar, starch and the like; disintegrators such as starch, carboxymethylcellulose, calcium salts of carboxymethylcellulose and the like; lubricants such as talc and the like; preservatives such as sodium benzoate, sodium bisulfite and the like; suspending agents such as methylcellulose, aluminum stearate, magnesium stearate and the like; and bases such as polyethylene glycol, Witepsol, white petrolatum and the like. According to the kinds of forms of the pharmaceutical composition, appropriate pharmaceutical agents are used.

The selenium-containing gold compound of the present invention can also be employed as an antidote for gold toxicity in the gold therapy of rheumatoid arthritis. It was found that the mice which have been received the selenium-containing gold compounds shows high resistance to the gold toxicity due to the administration of a gold compound, for example, $Na_3Au(S_2O_3)_2 \cdot 2H_2O$.

The following Examples illustrate the present invention in more detail but should not be construed as limiting the scope of the invention.

EXAMPLE 1

A number of experiments in which sodium selenite was given to mice both prior to and after treatment with a gold compound were conducted. In the first series of experiments in which the selenium compound was administered prior to the gold injection, mice were given sodium selenite in their drinking water over an extended period of time. Periodically, the mice were sacrificed and the kidney and liver were analyzed to monitor the accumulation of selenium. When observed selenium levels in the liver were on the order of 5 ppm, the remaining animals were given the gold compound at levels slightly exceeding the reported $LD_{50}$ value.

In the second series of experiments, in which sodium selenite were injected after the gold injection, the mice were given dosages of gold compounds at the reported $LD_{50}$ value and were then injected with sodium selenite. In both series of experiments, a control group which received the gold compound but no selenium compound was maintained. The result was that the mice which received selenium showed markedly reduced toxic effects from those which received only the gold treatment. This result supports our invention that the use of selenium compounds will mitigate or reduce the effect of gold toxicity. In all cases, the gold was administered as $Na_3Au(S_2O_3)_2 \cdot 2H_2O$.

EXAMPLE 2

In these experiments, large groups of mice were fed other type selenium compounds, which were sodium selenate, selenium yeast and selenocystine. Periodically, one would be sacrificed and the selenium concentration of the kidney and liver would be determined. When above 5 to about 7 ppm selenium concentrations were obtained, the remaining mice were given injections of $Na_3Au(S_2O_3)_2 \cdot 2H_2O$ at the reported $LD_{50}$ value. A control group that received no dietary selenium was maintained. This control group was given the gold salt at the same time as the selenium accumulated mice. The toxic effects of the gold was then compared in the two groups of mice.

In this set of experiments the mice that recieved selenium in their diet, followed by the administration of $Na_3Au(S_2O_3)_2 \cdot 2H_2O$ had a significantly lower mortality rate than the corresponding control group. The higher survival rate of the selenium group indicates that these selenium compounds also are effective in reducing gold toxicity.

EXAMPLE 3

Production of (tetra-O-acetyl-1-β-D-glucopyranosyl)seleno (triethylphosphine) gold

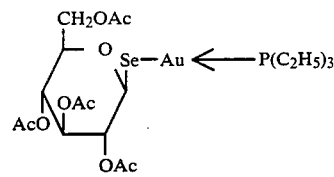

(Ac: acetyl group)

20.6 g of acetobromoglucose and 6.2 g of selenourea were refluxed in 100 ml of acetone, thereby obtaining (tetra-o-acetyl-1-β-D-glucopyranosyl)-2-selenoisourea hydrobromide. Then, 30 ml of an aqueous solution containing 5.88 g (0.011 mol of the above-obtained (tetra-O-acetyl-1-β-D-glucopyranosyl)-2-selenourea hydrobromide was prepared. To the solution was dropwise added 20 ml of an aqueous potassium carbonate solution containing 1.66 g (0.012 mol) of potassium carbonate at $-10°$ C. To the thus obtained solution was dropwise added 3.86 g (0.011 mol) of triethylphosphine gold chloride dissolved in ethanol containing a few drops of methylene chloride, and the obtained mixture was subjected to reaction for 30 minutes while cooling and stirring to form crystals. The crystals thus precipitated in the above-mentioned reaction mixture was separated by filtration. Then, the crystals were washed with water-ethanol and then with ethanol. Thus, there was obtained 0.007 mol of (tetra-O-acetyl-1-β-D-glucopyranosyl)-seleno (triethylphosphine) gold.

Elementary analysis (%) (as $C_{20}H_{34}AuO_9PSe$); Caluculated: C,33.13; H,4.69; Se,10.77; Found: C,33.21; H,4.71; Se,10.89.

EXAMPLE 4

Production of (1-β-D-glucopyranosyl)seleno (triethylphosphine) gold

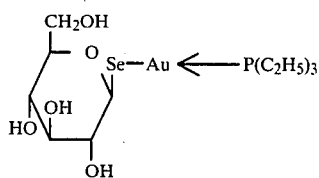

1.4 g (2 mmol)of (tetra-O-acetyl-1-β-D-glucopyranosyl) seleno (triethylphosphine) gold obtained in Example 3 was dissolved in 10 ml of absolute methanol. 540 mg (10 mmol) of $CH_3ONa$ was added to the thus obtained solution, and then stirred for 2 hours on ice. After completion of the reaction, the mixture was slightly acidified with 0.1N HCl. To the mixture was added 10 ml of water to form a precipitate. The thus obtained precipitate was separated by filtration and dried. Thus, 890 mg (1.6 mmol) of (1-β-D-glucopyranosyl)seleno (triethylphosphine) gold was obtained.

Elemental analysis (%) (as $C_{12}H_{26}O_5AuPSe$); Calculated: C,25.87; H,4.67; Se,14.17; Found: C,25.69; H,4.76; Se,14.28.

EXAMPLE 5

Production of triethylphosphine gold sodium selenomalate

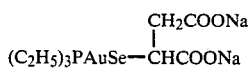

3.9 g of 2-bromo-2-deoxy-malic acid and 2.5 g of selenourea were boiled in 50 ml of acetone under reflux for one hour. Then, the mixture was cooled, thereby to form a precipitate. The precipitate was filtered off to obtain 2-selenoisourea malic acid hydrobromide

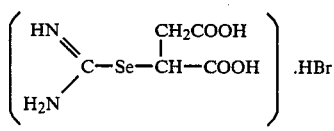

Then, 30 ml of an aqueous solution containing 3.2 g (10 mmol) of the above-obtained 2-selenoisourea malic acid hydrobromide was prepared. To the solution was dropwise added 20 ml of an aqueous potassium carbonate solution containing 2.04 g (22 mmol) of potassium carbonate at −10° C. To the thus obtained solution was dropwise added 3.51 g (10 mmol) of triethylphosphine gold chloride dissolved in ethanol containing a few drops of methylene chloride at −10° C., and then the mixture was stirred for 30 minutes while cooling, thereby to precipitate crystals. The crystals were filtered off and washed with water-ethanol, 0.1 N HCl and water, successively, thereby to obtain 3 g (6 mmol) of triethylphosphine gold selenomalate. The thus obtained triethylphosphine gold selenomalate was suspended in 20 ml of an aqueous solution containing 320 mg (3 mmol) of $Na_2CO_3$. The suspension was stirred for one hour and subjected to lyophilization. Thus, there was obtained 3 mmol of triethylphosphine gold sodium selenomalate.

Elemental analysis (%) (as $C_{10}H_{18}AuNa_2O_4PSe$); Calculated: C,21.64; H,3.24; Se,14.23; Found: C,21.73; H,3.28; Se,14.33.

The results of elemental analysis of 2-selenoisourea malic acid hydrobromide which was obtained as the intermediate in the production of triethylphosphine gold sodium selenomalate are shown below.

Elemental analysis (%) (as $C_5H_9N_2O_4BrSe$); Calculated: C,18.76; H,2.84; Se,24.67; Found: C,18.69; H,2.77; Se,24.81.

EXAMPLE 6

Production of [(phenylcarbamoyl) methyl]seleno (triethylphosphine)gold

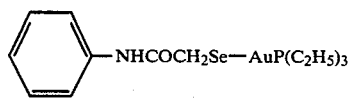

6.4 g of phenylcarbamoylmethyl bromide and 3.7 g of selenourea were boiled in 100 ml of acetone under reflux for one four. Then, the mixture was cooled, thereby to form a precipitate. The precipitate was filtered off to obtain phenylcarbamoylmethyl selenoisourea hydrobromide

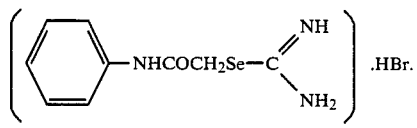

Then, 30 ml of an aqueous solution containing 3.4 g (10 mmol) of the above-obtained phenylcarbamoylmethyl selenoisourea hydrobromide was prepared. To the thus obtained solution was dropwise added 20 ml of an aqueous potassium carbonate solution containing 1.66 g (12 mmol) of potassium carbonate at −10° C. To the obtained solution was dropwise added 3.51 g (10 mmol) of triethylphosphine gold chloride dissolved in ethanol containing a few drops of methylene chloride at −10° C. and then, the mixture was stirred for one hour at −10° C. to precipitate crystals. The crystals were filtered off, washed with water-ethanol and water, successively, and dried. Thus, there was obtained 2.9 g (5.5 mmol) of [(phenylcarbamoyl) methyl]seleno (triethylphosphine) gold.

Elemental analysis (%) (as $C_{14}H_{23}NOAuPSe$); Calculated: C,31.84; H,4.36; Se,14.95; Found: C,31.91; H,4.44; Se,15.03.

The results of elemental analysis of phenylcarbamoylmethyl selenoisourea hydrobromide which was obtained as an intermediate in the production of [(phenylcarbamoyl) methyl]seleno (triethylphosphine) gold are shown below.

Elemental analysis (%) (as $C_9H_{12}N_3OBrSe$); Calculated: C,32.06; H,3.59; Se,23.42; Found: C,32.13; H,3.68; Se,23.56.

What is claimed is:

1. A selenium-containing gold compound having the general formula:

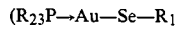

wherein
R₁ stands for
an unsubstituted or substituted glucose radical,
an unsubstituted or substituted malic acid radical,
an unsubstituted or substituted malate radical, or
an unsubstituted or substituted phenylcarbamoylmethyl radical; and
R₂ stands for a linear or branched alkyl group having 1 to 4 carbon atoms.

2. A selenium-containing gold compound according to claim 1, wherein R₁ stands for an unsubstituted or substituted glucose radical represented by

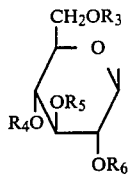

wherein R₃, R₄, R₅ and R₆ each independently stand for H, an acetyl group, a propionyl group or a butyryl group.

3. A selenium-containing gold compound according to claim 2, wherein R₁ stands for a 2,3,4,6-tetra-O-acetyl-1-β-D-glucopyranosyl radical represented by

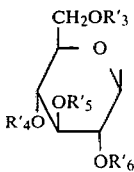

wherein R'₃, R'₄, R'₅ and R'₆ each stand for an acetyl group and R₂ stands for an ethyl group.

4. A selenium-containing gold compound according to claim 2 wherein R₁ stands for a 1-β-D-glucopyranosyl radical represented by

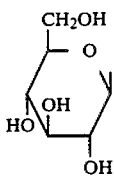

and R₂ stands for an ethyl group.

5. A method of treating a patient suffering from rheumatoid arthritis, which comprises administering to a petient an effective amount of a selenium-containing gold compound according to claim 1.

* * * * *

UNITED STATES PATENT AND TRADEMARK OFFICE
CERTIFICATE OF CORRECTION

PATENT NO. : 4,680,286
DATED : July 14, 1987
INVENTOR(S) : RICHARD F. STOCKEL ET AL It is certified that error appears in the above-identified patent and that said Letters Patent is hereby corrected as shown below:

Column 14, line 67: "$(R_{23}P \rightarrow Au - Se - R_1$" should read --- $(R_2)_3P - Au - Se - R_1$ ---.

Column 15, line 10: after "atoms" insert --- , and which is capable of self-detoxifying gold toxicity ---.

Column 15, line 16: on the right side of the formula, add --- (2) ---.

Signed and Sealed this

Third Day of May, 1988

Attest:

DONALD J. QUIGG

Attesting Officer

Commissioner of Patents and Trademarks